United States Patent [19]

Marhold et al.

[11] Patent Number: 4,885,388
[45] Date of Patent: Dec. 5, 1989

[54] 2-METHYL-4-FLUORO-PHENOLS AND THEIR PREPARATION

[75] Inventors: Albrecht Marhold, Leverkusen; Reiner Fischer, Monheim, both of Fed. Rep. of Germany

[73] Assignee: Bayer Aktiengesellschaft, Leverkusen, Fed. Rep. of Germany

[21] Appl. No.: 243,386

[22] Filed: Sep. 12, 1988

[30] Foreign Application Priority Data

Sep. 18, 1987 [DE] Fed. Rep. of Germany ....... 3731527

[51] Int. Cl.$^4$ ......................... C07C 85/11; C07C 37/00
[52] U.S. Cl. .................................... 564/417; 564/416; 564/418; 564/419; 568/709; 568/774
[58] Field of Search ........................ 568/709, 774, 775; 564/416, 417, 418, 419

[56] References Cited

U.S. PATENT DOCUMENTS

| 3,636,037 | 1/1972 | Donninger et al. | 568/709 |
| 3,903,178 | 9/1975 | Nakamura et al. | 564/417 |
| 4,217,304 | 8/1980 | Albrecht et al. | 564/417 |

FOREIGN PATENT DOCUMENTS

| 2001570 | 7/1971 | Fed. Rep. of Germany | 568/709 |
| 1246150 | 11/1986 | Japan | 568/775 |
| 2238226 | 10/1987 | Japan | 568/775 |

Primary Examiner—Werren B. Lone
Attorney, Agent, or Firm—Sprung Horn Kramer & Woods

[57] ABSTRACT

New 2-methyl-4-fluoro-phenols and process for their preparation from 2-methyl-4-fluoro-phenol.

16 Claims, No Drawings

2-METHYL-4-FLUORO-PHENOLS AND THEIR PREPARATION

New 2-methyl-4-fluoro-phenols of the formula (I)

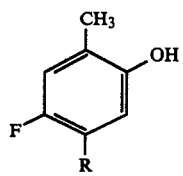

in which

R stands for $NO_2$ or $NH_2$ have been found.

These are 2-methyl-4-fluoro-5-nitrophenol and 2-methyl-4-fluoro-5-aminophenol.

A process for the preparation of compounds of the formula (I) has also been found, which is characterized in that the phenolic hydrogen atom in 2-methyl-4-fluorophenol is first replaced by a protecting group, a nitro group is then introduced at 0° to 40° C., then the protecting group is eliminated again by heating to reflux in the presence of water and acid and the nitro group thus introduced is optionally reduced to the amino group.

The 2-methyl-4-fluoro-phenol required for this process as a starting product is known and easily accessible (see, for example, J. Am. Chem. Soc. 81, 94 (1959)).

The first step of the process according to the invention, the replacement of the phenolic hydrogen atom in 2-methyl-4-fluoro-phenol by a protecting group, may take place, for example, in such a way that the hydrogen atom is replaced by a radical of the formulae (IIa) to (IIc)

 (IIa)

 (IIb)

 (IIc)

in which $R_1$ stands for $C_1$- to $C_4$-alkyl and, in the formulae (IIa) and (IIc), also for optionally substituted phenyl.

Such radicals can be introduced, for example, by reacting 2-methyl-4-fluoro-phenol, preferably in the presence of aqueous alkali and at temperatures from −20° to +100° C., with a compound which corresponds to one of the formulae (IIa) to (IIc) and contains a haogen atom, preferably a chlorine atom, on the free valency. Particularly preferably, 2-methyl-4-fluoro-phenol is reacted with methyl or ethyl chloroformate. The pure product may, for example, be isolated from the reaction mixture by extracting the reaction mixture with a solvent which is immiscible with water, for example a chlorinated hydrocarbon, drying the organic extract and fractionally distilling.

The second step of the process according to the invention, the introduction of a nitro group, may, for example, be carried out in such a way that the product from the first step is nitrated with mixed acid. The mixed acid may, for example, consist of a mixture of nitric acid of a concentration from 90 to 100% by weight with sulphuric acid of a concentration from 90 to 100% by weight, the weight ratio of nitric to sulphuric acid being, for example, in the range from 1:0.5 to 1:5.

The nitration is preferably carried out in the presence of a solvent, for example a chlorinated hydrocarbon. 1 to 1.2 moles of nitric acid in the form of the mixed acid may, for example, be employed relative to the product from the first step of the process according to the invention.

During the nitration, the temperature is kept in the range from 0° to 40° C. Preferably, the reaction is commenced at temperatures in the range 0° to 20° C. and led to completion at temperatures in the range 10° to 30° C. The working up of the nitration mixture may take place, for example, by pouring it onto ice, separating off the organic phase, if appropriate after adding a solvent which is immiscible with water, drying and fractionally distilling.

The third step of the process according to the invention, the elimination of the protecting group situated on the phenolic oxygen atom, is carried out in such a way that the product of the second step is heated to reflux in the presence of water and acid. Aqeuous hydrochloric acid, aqueous hydrobromic acid and aqueous sulphuric acid are, for example, suitable for this.

Preferably, the reaction is also carried out in the presence of a solvent, for example one having a boiling point in the range 50° to 120° C. (at atmospheric pressure).

After completion of the reaction, which is generally the case after 6 to 24 hours, the reaction mixture may be worked up, for example, as follows: it is first concentrated at reduced pressure, an extracting agent, for example an ether, is then added, the organic phase is then separated and washed intensively with aqueous alkali. After acidfying the aqueous/alkaline phase, 2-methyl-4-fluoro-5-nitrophenol then precipitates as a solid which can be recrystallized, for example, from toluene. As yet unhydrolysed product from the second step of the process according to the invention can optionally be recovered from the remaining organic phase.

For the preparation of 2-methyl-4-fluoro-5-aminophenol, if this is desired, the 2-methyl-4-fluoro-5-nitrophenol has still to be reduced. This reduction can take place in various ways, for example using iron or zinc as reductant. Preferably, the reduction is carried out catalytically using hydrogen. As catalysts, Raney nickel or noble metal, in particular palladium or platinum, catalysts may, for example, be used for this. The catalysts may contain the metals indicated in metallic form or in the form of compounds. They may also be supported catalysts in which metals and/or compounds are applied to a support material, for example to carbon, alumina, silica or silicates. If the reduction is carried out catalytically using hydrogen, the reaction is preferably carried out in the presence of a solvent, for example an alcohol such as methanol or ethanol, at temperatures from 20° to 50° C. and hydrogen pressures from 1 to 50 bar, and the reduction is carried out for a time such that the calculated amount of hydrogen is taken up.

The reaction mixture present after the reduction may be worked up, for example, by first separating the secondary products of the reductant, optionally together with excess reductant, or the catalyst, optionally evaporating off the solvent present and recrystallizing the residue remaining, for example from toluene.

It is not necessary to isolate and to purify the product present after each step. In particular, the nitro compound obtained in the second step can be processed further in the crude state.

The good accessibility of the new compounds 2-methyl-4-fluoro-5-nitrophenol and -5-aminophenol in the manner previously described was not to be expected, since in the nitration of the corresponding methoxy compound (containing a $CH_3-O-$ instead of an $HO-$ group) other isomers result (see Example 5).

The new compounds of the present invention (2-methyl-4-fluoro-5-nitrophenol=A; 2-methyl-4-fluoro-5-aminophenol=B) were characterized as follows:

|  | A | B |
|---|---|---|
| Melting point | 138–142°C. | 147° C. |
| $^1$H—NMR | 2.55 ppm $CH_3$ singlet (3H) | 2.13 ppm Ar—$CH_3$ singlet (3H) |
| in | 6.8 ppm CH doublet (1H) | 3.5 ppm $NH_2$, OH broad (3H) |
| $CDCl_3$(*) | 133 7.5 ppm CH doublet (1H) | 6.25 ppm ⎫ Ar—H doub- |
|  | 8.9 ppm OH singlet (1H) | 6.77 ppm ⎭ let (2H) |
| IR | 3350 cm$^{-1}$ OH | 3380 and 3300 cm$^{-1}$ $NH_2$ |
|  | 1520 cm$^{-1}$ $NO_2$ | 3500 to 2600 cm$^{-1}$ OH (broad) |
|  |  | 1640 cm$^{-1}$ C = C |
| MS | 171 m/e (base peak) 141 (24%), 95 (38%), 77 (42%) |  |

(*)Compound A at 60 MHz, compound B at 100 MHz.

The new compounds of the present invention are valuable intermediates for the preparation of particularly active herbicides and plant growth regulators of the formula (III)

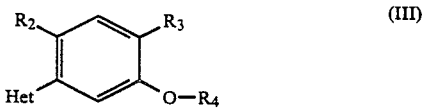

in which
Het stands for a heterocyclic ring of the formula

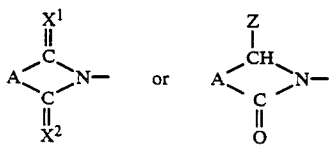

$R_2$ stands for hydrogen or halogen,
$R_3$ stands for alkyl and
$R_4$ stands for in each case optionally substituted alkyl, alkenyl, alkinyl or cycloalkyl, or for a radical

or a radical $-SO_2-R_6$,
where
A stands for a radical of the formula

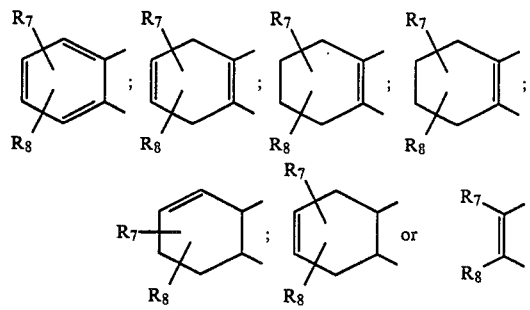

$X^1$ and $X^2$ in each case stand for oxygen or sulphur,
Z stands for hydrogen, hydroxyl or chlorine,
$R_5$ stands for alkyl, alkoxy or halogenoalkyl,
$R_6$ stands for alkyl, halogenoalkyl or for optionally substituted aryl and
$R_7$ and $R_8$ independently of one another in each case stand for hydrogen, halogen, alkyl or halogenoalkyl.

Compounds of the formula (III) can be obtained, for example, from the compounds of the formula (I) having $R=NH_2$, by reacting the compound of the formula (I) having $R=NH_2$ with anhydrides of the formula (IV)

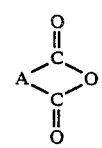

in which
A has the abovementioned meaning, and subsequently converting the phenolic OH groups into the $O-R_4$ groups using customary alkylating agents, acylating agents or sulphonylating agents.

EXAMPLES

Example 1

42 g of sodium hydroxide and 106 g of 2-methyl-4-fluoro-phenol were successively introduced into 660 ml of water. 108 g of methyl chloroformate were then added dropwise at +5° C. The mixture was stirred for 2 hours at +5° C., subsequently extracted using dichloromethane, and the organic phase was dried with sodium sulphate and subsequently fractionally distilled at reduced pressure. 139 g of (2-methyl-4-fluoro-phenyl)-methyl carbonate having a boiling point of 98° to 100° C. at 16 mbar and a refractive index $n_D^{20}$ of 1.4770 were obtained. The yield was thus 88% of theory.

Example 2

65 g of the product from Example 1 was introduced into 130 ml of dichloromethane and 65 g of mixed acid, prepared from 33% by weight nitric acid and 67% sulphuric acid (respective concentration 100%), were added dropwise at 20° C. The mixture was stirred for 2 hours at this temperature and finally for 1 hour more at 30° C. After cooling, the mixture was poured onto ice, and the organic phase was separated off and distilled. 62 g of (2-methyl-4-fluoro-5-nitrophenyl)-methyl carbonate having a boiling point from 120° to 125° C. at 0.27 mbar and a melting point of 68° C. were obtained. The yield was 76.6% of theory.

Example 3

156 g of the product from Example 2 were heated to reflux for 12 hours with 400 ml of dioxane and 300 ml of aqueous, 37% strength by weight hydrochloric acid. The cooled reaction mixture was subsequently concentrated under reduced pressure and the residue was taken up in methyl tert.-butyl ether. The ether phase was intensively washed with 400 ml of 10% strength by weight sodium hydroxide solution. The product, which was filtered and recrystallized from toluene, precipitated after acidifying the alkaline aqueous phase. It was 2-methyl-4-fluoro-5-nitrophenol having a melting point of 138° to 142° C. The yield amounted to 86 g, corresponding to 73.5% of theory.

Example 4

800 ml of ethanol were added to 54 g of the product from Example 3 and the mixture was reduced at 20° to 30° C. and a pressure of 5 bar after addition of 3 g of platinum dioxide. After taking up the calculated amount of hydrogen, the pressure was released, the catalyst was filtered off, the solvent was evaporated off in vacuo and the residue was recrystallized from toluene. 36.1 g of 2-methyl-4-fluoro-5-amino-phenol having a melting point of 147° C. were obtained. This corresponded to 81% of theory.

Example 5

(not according to the invention)

56 g of 2-methyl-4-fluoro-methoxy-benzene were introduced into 150 ml of dichloromethane at 10° C. and 85 g of nitrating acid (HNO₃ content 33%) were added dropwise in 30 minutes. The mixture was then stirred for 1 hour at 10° C. and 1 hour at 20° C. The reaction mixture was subsequently poured onto ice, extracted using dichloromethane, and the organic phase was separated off and distilled. The product passing over at 130° to 132° C. at 20 mbar was collected and filtered off with suction after stirring with 50 ml of n-hexane. 26 g of 2-methyl-3-nitro-4-fluoro-methoxy-benzene having a melting point of 38° to 40° C. were obtained.

What is clamed is:

1. 2-Methyl-4-fluoro-phenols of the formula

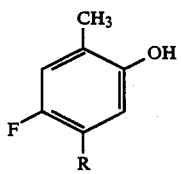

in which
R represents NO₂ or NH₂.

2. 2-Methyl-4-fluoro-5-nitro-phenol.
3. 2-Methyl-4-fluoro-5-amino-phenol.
4. A process for the preparation of 2-methyl-4-fluoro-5-nitrophenol comprising replacing a phenolic hydrogen atom in 2-methyl-4-fluorophenol by a protecting group by a reaction with a compound of one of the formulas

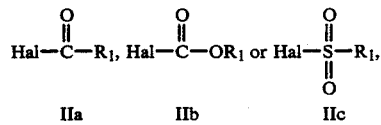

wherein
R₁ is C₁ to C₄-alkyl and in the case of formulas IIa and IIc,
R₁ is also substituted or unsubstituted phenyl and Hal is a halogen atom, introducing a nitro group at 0° to 40° C. comprising conducting nitration with a mixture comprising nitric acid of a concentration from 90 to 100% by weight and sulphuric acid of a concentration from 90 to 100% by weight, with a weight ratio of nitric acid to sulphuric acid in the range from 1:0.5 to 1:5 and then eliminating the protecting group by heating to reflux in the presence of water and acid.

5. A process for the preparation of 2-methyl-4-fluoro-5-aminophenol, comprising replacing a phenolic hydrogen atom in 2-methyl-4-fluorophenol by a protecting group by reaction with a compound of one of the formulas

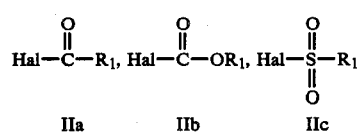

wherein
R₁ is C₁- to C₄-alkyl and in the case of formulas IIa and IIc, R₁ is also substituted or unsubstituted phenyl and Hal is a halogen atom, introducing a nitro group at 0° to 40° C. comprising conducting nitration with a mixture of nitric acid of a concentration from 90 to 100% by weight and sulphuric acid of a concentration from 90 to 100% by weight, with a weight ratio of nitric acid to sulphuric acid in the range from 1:0.5 to 1:5, eliminating the protecting group by heating to reflux in the presence of water and acid and reducing the nitro group to an amino group by conducting a reduction with a catalyst and a reductant selected from the group consisting of iron, zinc and hydrogen.

6. A process according to claim 5 in which the nitration is commenced at temperatures in the range 0° to 20° C. and led to completion at temperatures in the range 10° to 30° C.

7. A process according to claim 5 wherein the nitration is commenced at a temperature of 0° to 20° C. and is led to completion at a temperature of 10° to 30° C.

8. A process according to claim 4, wherein the replacing of the phenolic hydrogen atom occurs at −20° to +100° C.

9. A process according to claim 5, wherein the replacing of the phenolic hydrogen atoms occurs at −20° to +100° C.

10. A process according to claim 4, wherein the replacing of the phenolic hydrogen occurs in the presence of aqueous alkali.

11. A process according to claim 5, wherein the replacing of the phenolic hydrogen occurs in the presence of aqueous alkali.

12. A process according to claim 4, wherein Hal is chlorine.

13. A process according to claim 5, wherein Hal is chlorine.

14. A process according to claim 4, wherein in eliminating the protecting group the acid is an acid selected from the group consisting of hydrochloric acid, hydrobromic acid and sulphuric acid.

15. A process according to claim 5, wherein in eliminating the protecting group the acid is an acid selected from the group consisting of hydrochloric acid, hydrobromic acid and sulphuric acid.

16. A process according to claim 5, wherein the catalyst is Raney nickel or a noble metal.

* * * * *